United States Patent [19]
Vernick

[11] Patent Number: 5,203,786
[45] Date of Patent: Apr. 20, 1993

[54] HEPATIC RESECTION CLAMP

[75] Inventor: Jerome J. Vernick, Philadelphia, Pa.

[73] Assignee: Thomas Jefferson University, Philadelphia, Pa.

[21] Appl. No.: 717,801

[22] Filed: Jun. 19, 1991

[51] Int. Cl.[5] ............................................. A61B 17/00
[52] U.S. Cl. ................................... 606/151; 24/280; 24/20 EE; 24/274 WB
[58] Field of Search ............... 606/151, 157, 158, 203; 24/20 R, 22 EE, 274 WB, 275, 280, 276–279

[56] References Cited

U.S. PATENT DOCUMENTS

| | | | |
|---|---|---|---|
| 3,095,873 | 7/1963 | Edmunds | 606/203 |
| 3,667,471 | 6/1972 | Doty et al. | 606/158 |
| 3,747,172 | 7/1973 | Tarzian | 24/282 |
| 3,840,018 | 10/1974 | Heifetz | 606/158 |
| 4,286,361 | 9/1981 | MacKenzie | 24/276 |
| 4,521,940 | 6/1986 | Oetiker | 24/282 |
| 4,821,720 | 4/1989 | Hajduch | 606/157 |

FOREIGN PATENT DOCUMENTS 3047723 7/1982 Fed. Rep. of Germany ...... 606/228

Primary Examiner—Stephen C. Pellegrino
Assistant Examiner—Gary Jackson
Attorney, Agent, or Firm—Woodcock, Washburn, Kurtz, MacKiewicz & Norris

[57] ABSTRACT

A novel surgical clamp is provided for application to the liver, comprising an upper flexible band and a lower base, which are attached at their distal end. The proximal end of the lower base terminates in a handle. A worm drive apparatus for receiving the proximal end of the upper band is slidably mounted on the lower base. Clamping is accomplished by positioning the slidable worm drive apparatus, such that the length of the lower base between the apparatus and the distal end conforms to the inferior surface of the liver, and then gradually engaging the upper band with the worm drive apparatus, such that the upper band is compressed toward the lower base.

10 Claims, 1 Drawing Sheet

HEPATIC RESECTION CLAMP

BACKGROUND OF THE INVENTION

The present invention relates to the field of surgical instruments and particularly to surgical clamps.

Major resections of the liver require divisions of large veins and thick vascular tissue. It is not always possible to ligate these structures prior to cutting them, and uncontrollable intra-operative bleeding is a major complication. Occlusion clamps, which can isolate the portion of the liver to be resected, provide major improvements in the success and speed of these operations.

U.S. Pat. No. 4,286,361 to MacKenzie; U.S. Pat. No. 3,747,172 to Tarzian; and U.S. Pat. No. 4,521,940 to Oetiker teach hose clamps. U.S. Pat. No. 3,840,018 to Heifetz and U.S. Pat. No. 4,821,720 to Hajduch teach clamps for medical tubing. These clamps are all intended for clamping tubular structures. Such clamping is accomplished through a single band, which is formed into a circle, and tightened to clamp the tubular structure. None of these clamps are applicable to clamping organs such as the liver, which are not tubular in structure.

Doty et al. in U.S. Pat. No. 3,667,471 teaches a liver clamp comprising a rigid elongated base member supporting two flexible foam rubber covered blades and a means for independent adjustment of each blade. A handle is attached to one end of the clamp base. There are several limitations in this design. The construction is complex, consisting of multiple moving parts requiring sophisticated machining. The clamp requires multiple steps to use in that the inferior and superior blades must be prepositioned and then the superior blade tightened and the interior blade compressed in order to use the clamp. The rigid base, in addition to the movable blades, makes the clamp more cumbersome. Also the blade is not readily adaptable to different size livers, because of the fixed length of the inferior blade. The clamp will not evenly compress the entire line of resection, but will compress the center more than the ends, because of the fixed length of the inferior and superior blades between the two points where they meet. This uneven compression often results in bleeding at the ends of the liver, where there is the least compression.

The Longmire-Storm clamp (V. Mueller, Stainliss, Germany, catalogue # SU-9080) is one of the earliest devices used in liver resection. Like the Doty clamp, it comprises flexible upper and lower bands of fixed length which are attached at both ends. However, because of its fixed size, it is not usable with all livers, and like the Doty clamp, it does not evenly compress the entire line of resection on those livers where it is usable, resulting in bleeding at the ends of the liver.

Accordingly, a need exists for a surgical clamp adaptable to different sized organs, capable of applying evenly distributed pressure.

SUMMARY OF THE INVENTION

The present invention is a surgical clamp for application to organs of varying shapes and sizes, including the liver. The invention comprises an upper flexible band and a lower rigid base attached at one end. For reference purposes, the attached ends of the lower base and upper band are called the distal ends and the other ends are called the proximal ends. In a preferred embodiment, the proximal end of the lower base terminates in a handle. Clamp adjusting means are slidably mounted on the lower base and have engaging means for gradually engaging the proximal end of the upper band such that the upper band is compressed toward the lower base. In a preferred embodiment, at least a portion of the upper band has evenly spaced apertures therethrough. In a preferred embodiment, the engaging means comprise a housing for receiving the proximal end of the upper band with a worm screw with threads rotatably mounted therein in alignment with the upper band such that as the screw is rotated the screw threads engage the apertures on the upper band to compress the clamp.

Because the length of the lower base being applied to the organ being clamped can be controlled by positioning the clamp adjusting means, and the length of the upper band being applied to the organ being clamped can be controlled by the engaging means, the clamp is applicable to organs of varying shapes and sizes. The design of the clamp also provides for more even distribution of pressure on the organ being clamped.

Accordingly, a primary object of the present invention is the provision of a novel surgical clamp capable of effectively clamping organs of varying shapes and sizes, with an even distribution of pressure on the organ.

This and other objects of the present invention will become apparent from the following, more detailed description of the present invention.

DESCRIPTION OF THE PREFERRED EMBODIMENT

Figure 1:
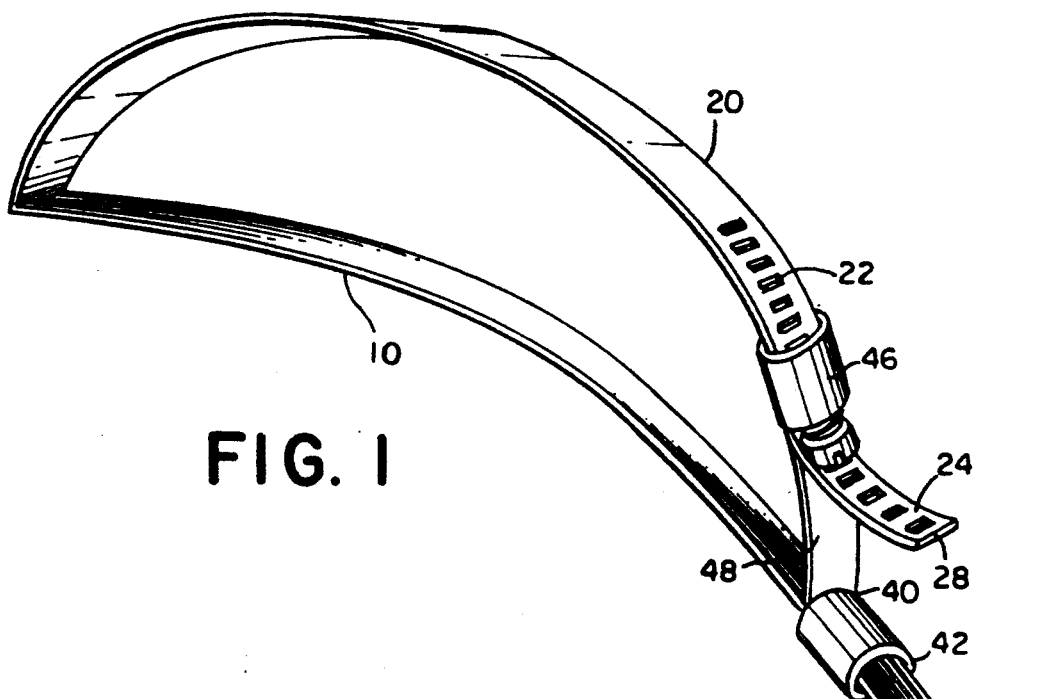
FIG. 1 is a perspective view illustrating a surgical clamp in accordance with the present invention.

The invention is a surgical clamp capable of effectively clamping organs of varying shapes and sizes. Referring to FIG. 1, there is shown a rigid lower base 10, and a flexible upper band 20, preferably having a plurality of evenly spaced apertures therethrough 22. The base 10 and band 20 are preferably formed of stainless steel. The length of the base 10 is shaped to conform to the lower surface of the liver or other organ (not shown). The top surface of the lower base 10 is rounded. The base 10 is preferably about 5 mm thick and about 12 mm wide. The band 20 is preferably about 0.5 mm thick and about 10 mm wide. For a clamp to be used for clamping an adult liver, the base is about 200 mm long. For a clamp to be used for clamping a child's liver, the base may be shorter. The length of the band is preferably about one and a half times the length of the base. One end of the lower base terminates in a handle 30. For reference purposes, the ends of the lower base and upper band closest to the handle 30 are called the proximal ends, and the ends furthest from the handle are called the distal ends. The upper band's distal end is welded to the lower base's distal end. In other embodiments, the distal ends may be connected by a hinge or other means.

Figure 2:
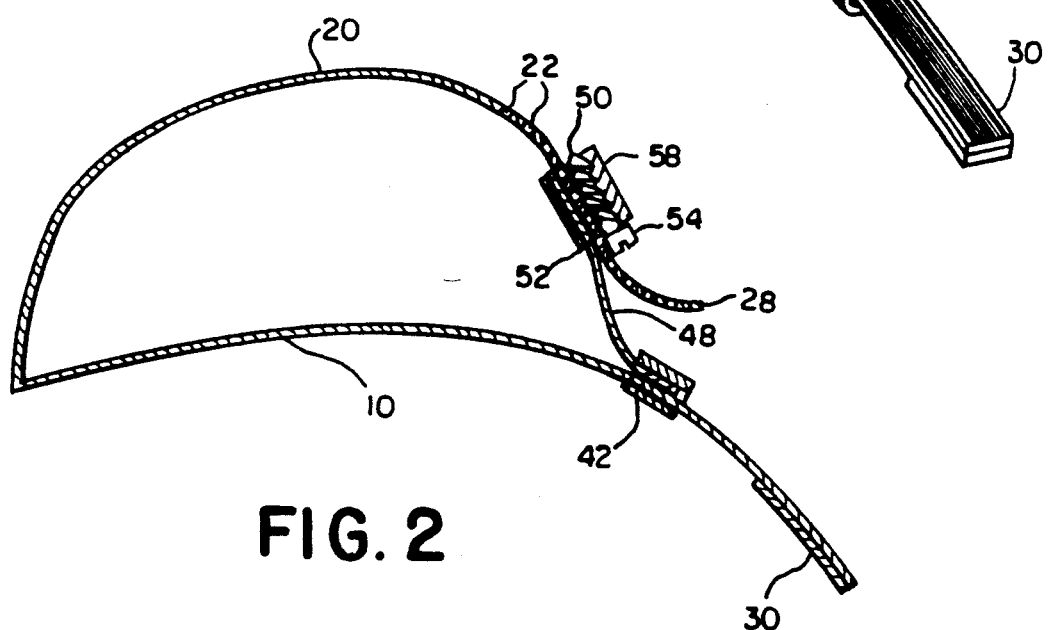
FIG. 2 is a cross-sectional side elevation view of the surgical clamp taken transversely down its center.

A clamp adjusting means 40 is slidably mounted on the lower base 10. The clamp adjusting means 40 comprises a clip 42 which is adapted to slide along the lower base 10. The clamp adjusting means 40 further preferably comprises a worm drive apparatus 46 attached to the clip by a band section 48. The worm drive apparatus 46 is a standard product which is generally available, and its use and operation are well known to those of ordinary skill. Referring to FIG. 2, the worm drive apparatus 46 comprises a housing 58 having two openings 50, 52 for the upper band 20 to enter and exit. The housing engages a screw 54 aligned with the housing openings 50, 52. In operation, the proximal end 28 of the upper band 20 is introduced into the housing opening 50 until the upper band apertures initially are engaged by the screw 54. The screw 54 is then turned to move the upper band 20 through the housing, the excess emerging from the housing opening 52. Thus, as the screw 54 is moved in this direction, the clamp constricts around the organ; by rotating the screw 54 in the reverse direction, clamping pressure is relieved. Prior to using the clamp, the upper band and lower base may be covered with a cotton stockinette or other padding to provide a softer surface with better traction for clamping the liver.

To operate the clamp, the clip 42 is moved to a position such that the length of the lower base 10 between the clip 42 and the distal end of the lower base 10 is slightly longer than the inferior surface of the organ to be clamped. The proximal end 28 of the upper band 20 is then introduced into the worm drive apparatus 46 and the screw 54 is turned until the area between the upper band and the lower base is somewhat larger than the organ to be clamped. The clamp is then positioned around the organ, and the screw 54 is tightened until the organ is sufficiently clamped. To disengage the clamp, the screw is turned counterclockwise until the clamp is sufficiently loosened to remove it.

The invention is further described in the following example, which is not meant to be limiting.

EXAMPLE 1

A clamp in accordance with the present invention was fabricated as described in the detailed description and has been used in fifteen liver resections, including resections of livers too large to be clamped with the Longmire-Storm clamp. Bleeding during the resections has been minimal, including at the ends of the liver.

While specific forms of the present invention have been selected for the purposes of illustration, one of ordinary skill in the art will recognize that various departures may be made to the examples set forth herein without departing from the scope of the present invention, which is defined more particularly in the appended claims.

What is claimed is:

1. A clamp comprising:
   an upper flexible band and a lower base, each having proximal and distal ends, said band and base being attached to each other at their distal ends; and
   clamp adjusting means attached to said upper flexible band slidably mounted on said lower base such that the portion of said lower base between the distal end of said lower base and the clamp adjusting means may be varied, said clamp adjusting means having engaging and retracting means for gradually engaging and retracting the proximal end of said upper band past or through said engaging and retracting means, whereby the portion of said upper band between the distal end of said upper band and the engaging and retracting means may be varied.

2. The clamp of claim 1 further comprising a handle at said proximal end of said lower base.

3. The clamp of claim 1 wherein said upper band has a plurality of apertures therethrough for at least a portion of the length thereof.

4. The clamp of claim 3 wherein said engaging and retracting means comprises a housing for receiving the proximal end of said upper band, having a worm screw with threads rotatably mounted therein in alignment with said upper band, whereby as said screw is rotated the screw threads engage said apertures on said upper band to retract said upper band and compress the clamp.

5. The clamp of claim 1 wherein said band and base are comprised of stainless steel.

6. The clamp of claim 1 further comprising a covering over a portion of said base and band for creating a padded surface.

7. The clamp of claim 6 wherein said covering is cotton.

8. A surgical clamp comprising:
   a base and a band, each having proximal and distal ends, being affixed at their distal ends and defining a clamping circumference therebetween; and
   clamp adjusting means attached to said upper flexible band for slidably connecting the proximal end of the band to the base such that the portion of said base between the distal end of said base and the clamp adjusting means may be varied, said clamp adjusting means further comprising means for retracting the band whereby the portion of said band between the distal end of said band and the clamp adjusting means may be varied to constrict the clamping circumference.

9. The clamp of claim 8 further comprising a handle affixed to the proximal end of the base.

10. A clamp comprising:
    an upper flexible band and a lower base, each having proximal and distal ends, said upper flexible band and lower base being attached to each other at their distal ends and connected at their proximal ends so as to define clamping lengths and for each of said upper flexible band and said lower base; and
    clamping adjusting means attached to said upper flexible band slidably mounted on said lower base such that the clamping length of said lower base and the arc of said upper flexible band can be varied by varying the distance between the distal and proximal ends of the upper flexible band and the lower base, said clamp adjusting means also comprising means for varying the clamping length of said upper flexible band, thereby varying the arc of said upper flexible band,
    whereby an arc created by said upper flexible band in relation to the lower base can be varied either by varying the clamping length of the upper flexible band or by varying the clamping length of the lower base.

* * * * *

UNITED STATES PATENT AND TRADEMARK OFFICE
CERTIFICATE OF CORRECTION

PATENT NO. : 5,203,786
DATED : APRIL 20, 1993
INVENTOR(S) : JEROME J. VERNICK

It is certified that error appears in the above-indentified patent and that said Letters Patent is hereby corrected as shown below:

Column 4, line 47, "clamping" should be "clamp".

Signed and Sealed this

Fifteenth Day of March, 1994

Attest:

BRUCE LEHMAN

Attesting Officer     Commissioner of Patents and Trademarks